(12) United States Patent
Narvel et al.

(10) Patent No.: US 8,198,509 B2
(45) Date of Patent: Jun. 12, 2012

(54) METHODS AND COMPOSITIONS FOR SELECTING SOYBEAN PLANTS RESISTANT TO SOUTHERN ROOT KNOT NEMATODE

(75) Inventors: James Narvel, Middletown, DE (US); Vergel Concibido, Maryland Heights, MO (US); Liesa Cerny, Chesterfield, MO (US); John Tamulonis, Nevada, IA (US); Floyd Hancock, Stuttgart, AR (US); Richard Dougherty, Kinston, NC (US); Henry Roger Boerma, Athens, GA (US); Bo-Keun Ha, Athens, GA (US)

(73) Assignees: Monsanto Technology LLC, St. Louis, MO (US); University of Georgia Research Foundation, Athens, GA (US)

( * ) Notice: Subject to any disclaimer, the term of this patent is extended or adjusted under 35 U.S.C. 154(b) by 716 days.

(21) Appl. No.: 12/186,703

(22) Filed: Aug. 6, 2008

(65) Prior Publication Data

US 2009/0064354 A1    Mar. 5, 2009

Related U.S. Application Data

(60) Provisional application No. 61/055,519, filed on May 23, 2008, provisional application No. 60/963,836, filed on Aug. 7, 2007.

(51) Int. Cl.
*A01H 5/00* (2006.01)
*A01H 1/02* (2006.01)
*A01H 1/00* (2006.01)
*C12N 5/00* (2006.01)
*C12N 5/04* (2006.01)

(52) U.S. Cl. ........ 800/265; 800/260; 800/266; 800/267; 800/279; 800/312; 435/468

(58) Field of Classification Search .................. None
See application file for complete search history.

(56) References Cited

U.S. PATENT DOCUMENTS

| | | |
|---|---|---|
| 2004/0031072 A1 | 2/2004 | La Rosa et al. |
| 2005/0278804 A1 | 12/2005 | Hoogstraten et al. |
| 2006/0288444 A1 | 12/2006 | McCarroll et al. |

OTHER PUBLICATIONS

Luzzi, BM, et al. Resistance to Three Species of Root-Knot Nematode in Soybean, Crop Science, 27: 258-262. Mar.-Apr. 1987.
Tamulonis, JP, et al. RFLP Mapping of Resistance to Southern Root-Knot Nematode in Soybean, Crop Science, 37: 1903-1909. Nov.-Dec. 1997.
Ha, B; et al. Pedigree Analysis of a Major QTL Conditioning Soybean Resistance to Southern Root-Knot Nematode, Crop Science, 44: 758-763. May-Jun. 2004.
Ha, B; et al. Development of SNP Assays for Marker-Assisted Selection of Two Southern Root-Knot Nematode Resistance QTL in Soybean, Crop Science, 47: S-73-S-82. Jul. 2007.
Ha et al., Pedigree Analysis of a Major QTL Conditioning Soybean Resistance to Southern Root-Knot Nematode, Crop Science 44:758-763 (2004).
Ha et al., Development of SNP Assays for Marker-Assisted Selection of Two Southern Root-Knot Nematode Resistance QTL in Soybean, Crop Science 47:S73-S82 (2007).
Collard et al., An introduction to markers, quantitative trait loci (QTL mapping and marker-assisted selection for crop improvement: The basic concepts, Euphytica 142:169-196 (2005).
Tamulonis et al., RFLP Mapping of Resistance to Southern Root-Knot Nematode in Soybean, Crop Science 37:1903-1909 (1997).
Database Geneseq, Mar. 22, 2007, Soybean (Glycine max) polymorphic DNA sequence, Database Accession No. AEM75704.
Database Geneseq, Oct. 18, 2007, Glycine max cDNA, Database Accession No. AFP15229.

*Primary Examiner* — Medina A Ibrahim
(74) *Attorney, Agent, or Firm* — James E. Davis; Thomas P. McBride

(57) ABSTRACT

The present invention is in the field of plant breeding and disease resistance. More specifically, the invention includes a method for breeding soybean plants containing one or more quantitative trait loci (QTL) associated with resistance to Southern Root Knot Nematode (SRKN). The invention further provides germplasm and the use of germplasm containing QTL conferring disease resistance for introgression into elite germplasm in a breeding program, thus producing novel elite germplasm comprising one or more SRKN resistance QTL.

17 Claims, 2 Drawing Sheets

| Marker | Chromosome Position (cM) | SEQ ID | Resistance Allele[1] | Susceptible Allele | SEQ ID Forward Primer | SEQ ID Reverse Primer | SEQ ID Probe 1 | SEQ ID Probe 2 | SEQ ID Res. Allele | SNP Position[2] |
|---|---|---|---|---|---|---|---|---|---|---|
| NS0094902 | 1.6 | 1 | ************ | TTATCAATTAT | 5 | 6 | 13 | 14 | 21 | 285-295 |
| NS0097935 | 2.7 | 2 | G | C | 7 | 8 | 15 | 16 | 22 | 346 |
| NS0135583 | 3.1 | 3 | C | T | 9 | 10 | 17 | 18 | 23 | 730 |
| NS0102683 | 17.9 | 4 | A, G | -- | 11 | 12 | 19 | 20 | 24, 25 | 320 |

[1] "*" indicates a single nucleotide deletion
[2] SNP Position: refers to the position of the SNP polymorphism in the indicated SEQ ID number.

FIGURE 1

| Marker | Chr Pos. (cM) | SEQ ID Marker | Res. Allele(1) | Susc. Allele(1) | Res. Allele(2) | Susc. Allele(2) | SEQ ID Forward Primer | SEQ ID Reverse Primer | SEQ ID Probe 1 | SEQ ID Probe 2 | SEQ ID Res. Allele | SNP[1] Position (1) | SNP[1] Position (2) |
|---|---|---|---|---|---|---|---|---|---|---|---|---|---|
| SNP358 | 5.3 | 26 | T | A | A | G | 28 | 29 | 32 | 33 | 36 | 83 | 91 |
| SNP199 | 63.8 | 27 | A | T | A | G | 30 | 31 | 34 | 35 | 37 | 202 | 209 |

[1]SNP Position: refers to the position of the SNP polymorphism in the indicated SEQ ID NO.

FIGURE 2

SEQUENCE LISTING

<160> NUMBER OF SEQ ID NOS: 45

<210> SEQ ID NO 1
<211> LENGTH: 532
<212> TYPE: DNA
<213> ORGANISM: Glycine max

<400> SEQUENCE: 1

| | | | | | |
|---|---|---|---|---|---|
| gctcaatcaa | gtacacccat | catccttctt | ctcttcacgc | ctagcactca | aatttgtagc | 60 |
| gcatgctata | actattaact | aaccctctgt | cccttcttgc | aacaattgca | acctccttcc | 120 |
| ttccactctt | ttcccatcat | cattccacac | ctacctttct | ctctccccca | tgttttaact | 180 |
| ttcttcaaca | ctcactgact | tttccactat | ctcttccttc | ttccattcac | atcattttct | 240 |
| cttccttctt | cctcccccct | tttgttgttg | ttgttgttgt | ttatttatca | attatcacca | 300 |
| tgcccctcaa | acaattcaac | caaagcttgc | aactttgaca | accctttggc | ctcttcttct | 360 |
| tgttcccctt | aatgggtctc | tctccaattc | ccctcacaaa | gcctatctat | tctgatgtct | 420 |
| gaatttcact | ttggttttca | tatgttccca | aaggctacac | ctttgcgggt | gtagaagtgg | 480 |
| ataatttcag | agttttgggg | acaccccatt | ttgaagaaag | tgtgtgtgtg | tg | 532 |

<210> SEQ ID NO 2
<211> LENGTH: 703
<212> TYPE: DNA
<213> ORGANISM: Glycine max
<220> FEATURE:
<221> NAME/KEY: unsure
<222> LOCATION: (693)..(693)
<223> OTHER INFORMATION: n = a,t,c,or g
<220> FEATURE:
<221> NAME/KEY: unsure
<222> LOCATION: (1)..(703)
<223> OTHER INFORMATION: unsure at all n locations

<400> SEQUENCE: 2

| | | | | | |
|---|---|---|---|---|---|
| attagatggt | agttgaagca | atctgccttt | gaactcttct | tctggctcag | catgcatgct | 60 |
| tgtgttcata | ctattactat | atccacctct | ctttatgtct | cattctatt | cgtaagtatt | 120 |
| tgatattgaa | ttttggataa | tgattatttg | ctgcaatagc | cactttgagc | ttagggagaa | 180 |
| cttttctatt | ctttgatggc | tgcaataact | gcatatggca | ttttaatata | gtttgataat | 240 |
| aatgtaagag | atgggggacc | tggacggctg | gacccggtaa | tggcaaagac | aatttctttt | 300 |
| agaaaaatt | aattaggaca | tttcgttttg | tcacaagaga | aaagtgaatc | ttaatgtatg | 360 |
| taatagataa | tgccacaaga | aaaaattaaa | aaactagaaa | aactaaggcc | ttctatcggt | 420 |
| cagttgacct | caaaatacgt | actcgagtac | tgtacattcg | gatgttggag | gtataaatta | 480 |
| aaagtcattt | ttaatttata | tttatcatta | gtgttgagat | aaaattgaat | tattcaactt | 540 |
| gagaaaatga | ttgataattc | agttggattg | ccccctttgac | ttgtatgctt | gcgtatattg | 600 |
| gtatgaaatc | aaatatgcca | aatattatca | tcattgaaat | aaccttttga | tattgatagg | 660 |
| gtacttaatt | atttcaagaa | ttgttgtgtg | ctngttaatc | ctt | | 703 |

<210> SEQ ID NO 3
<211> LENGTH: 792
<212> TYPE: DNA
<213> ORGANISM: Glycine max

```
<400> SEQUENCE: 3
tttccttgaa ggtttacttc aacgtggttt ggaaagattt gctacattcg ccaaaagcta      60
cacctaaatt tttattatga ttgtcctgat ttttatagca gggctacatt tctaaaagtg     120
aacatacctg attattttca tggcgatctc attctgtctg aacattgatt gaattactgt     180
tatcatgcca attttggtt gcatgaatgg ttatcccatt ttgaagtgtt aattaattat      240
gtataactct gatagacggt cttaatgcaa aatgaacaca tccgacataa tgttaaaggt     300
ctgttcttaa atccgcaatc ctaaatttgt aacgctgctt tgagcacttc agaaatgatt     360
ggatttggat cctagcaagt aaaatttgcc aaaccatctc gaaacttaag ctccagagtc     420
ctatgcggag tatatagata catgtcctaa atgagtata tgtaattgct aacagataat      480
ggaatagaag ctaagagatt ccatttattg acgcacaaga atctgacatg aatgtggcag     540
tcatagtaaa aattgactat agtacaaaat aataatgtaa cgacaacaca tatttacacc     600
accatcctcc aacccaggct acgtacatca accgaccacg taaaaaatg atggcagctt      660 tttccaatgt ctaaactgaa gcaaccgaaa acagtgtgta taatcccaac aacacattat     720
tagatgaacc gtgtatgtac atacattcag ttgcttgcac tgccttccaa caagctcctc     780
aagctacaaa ga                                                         792

<210> SEQ ID NO 4
<211> LENGTH: 835
<212> TYPE: DNA
<213> ORGANISM: Glycine max
<220> FEATURE:
<221> NAME/KEY: unsure
<222> LOCATION: (692)..(692)
<223> OTHER INFORMATION: n = a,t,c, or g
<220> FEATURE:
<221> NAME/KEY: unsure
<222> LOCATION: (1)..(835)
<223> OTHER INFORMATION: unsure at all n locations

<400> SEQUENCE: 4
gagaaactgc cttagcaaga aatatggcac ggagagcaaa ctgagctgta tgttgttggg      60
atggctccaa ttgccaatca tactctgtaa ctgaatatgt gaagagaacg aggttgaaaa     120
tatagaaaac cactttccac gtggcaaatg agcagaggta tagtattcga tcaagcacaa     180
tcaagaagaa gatagcctga acagaagaag taactcttat taggagtgta tatgacatga     240
caactctagc cacacttata aatgaaacat gcaataaatc attgcgtcac tctaacatat     300
gtattcaaca aagaaacgtg gataagaaat gtttcctaaa catgtcaatg atgaattaca     360
gtcattctct ttcgaagtgc tacaaatttt aacctccaaa ttatgaaaag gaaaacaaaa     420
tcttaatgtt tcattccatt tggaaaacaa aatgtatcat aaatgaaatc atttcaaagg     480
ttctggacaa tttcttggca ttataaacaa catgaatttt atattagatc tctaacatcc     540
cccctgtaca ggcccttgg gtttgaaaaa gggaatatgc tgacctacca tgtgctgaaa      600
ttcaacattt ttttagaatg acagacaaca aggatcaaac tctagactac atacttggtc     660
aaagaacctc taataccaca tcaggaacca ancactccat aagcttaagc tgttagatga     720
agagatatga atagttgtac actacgtctc taacaattgg cacacttgac ctgctttgtt     780
taccccataa aagtcaaatt tgtctgaatg aattaaattc ttttttaagcc ctgtt          835

<210> SEQ ID NO 5
<211> LENGTH: 21
<212> TYPE: DNA
<213> ORGANISM: Artificial Sequence
```

```
<220> FEATURE:
<223> OTHER INFORMATION: Other information: Description of artificial
      sequence: synthetic primer

<400> SEQUENCE: 5
tcctccccct ttttgttgtt g                                              21

<210> SEQ ID NO 6
<211> LENGTH: 22
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 6
tgcaagcttt ggttgaattg tt                                             22

<210> SEQ ID NO 7
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 7
aaattaatta ggacatttcg ttttgtca                                       28

<210> SEQ ID NO 8
<211> LENGTH: 29
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 8
ctagtttttt aattttttct tgtggcatt                                      29

<210> SEQ ID NO 9
<211> LENGTH: 27
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 9
aaaacagtgt gtataatccc aacaaca                                        27

<210> SEQ ID NO 10
<211> LENGTH: 20
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 10
ggaaggcagt gcaagcaact                                                20

<210> SEQ ID NO 11
<211> LENGTH: 28
<212> TYPE: DNA
<213> ORGANISM: Artificial Sequence
```

-continued

```
<220> FEATURE:
<223> OTHER INFORMATION: Other information: Description of artificial
      sequence: synthetic primer

<400> SEQUENCE: 11
cattgcgtca ctctaacata tgtattca                                           28

<210> SEQ ID NO 12
<211> LENGTH: 28
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 12
tgtaattcat cattgacatg tttaggaa                                           28

<210> SEQ ID NO 13
<211> LENGTH: 15
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 13
tttatcacca tgccc                                                         15

<210> SEQ ID NO 14
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 14
ttgttgttgt ttatttatc                                                     19

<210> SEQ ID NO 15
<211> LENGTH: 18
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 15
caagagaaaa gtcaatct                                                      18

<210> SEQ ID NO 16
<211> LENGTH: 18
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 16
caagagaaaa gtgaatct                                                      18

<210> SEQ ID NO 17
<211> LENGTH: 15
<212> TYPE: DNA
<213> ORGANISM: Artificial Sequence
```

```
<220> FEATURE:
<223> OTHER INFORMATION: Other information: Description of artificial
      sequence: synthetic probe

<400> SEQUENCE: 17
tacacggttc atcta                                                          15

<210> SEQ ID NO 18
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 18
tgtacataca cagttcatc                                                      19

<210> SEQ ID NO 19
<211> LENGTH: 18
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 19
caaagaaacg tagataag                                                       18

<210> SEQ ID NO 20
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 20
aaacgtggat aagaaa                                                         16

<210> SEQ ID NO 21
<211> LENGTH: 34
<212> TYPE: DNA
<213> ORGANISM: Glycine max

<400> SEQUENCE: 21
tgttgttgtt gtttatcacc atgccctca aaca                                      34

<210> SEQ ID NO 22
<211> LENGTH: 35
<212> TYPE: DNA
<213> ORGANISM: Glycine max

<400> SEQUENCE: 22
gtcacaagag aaaagtgaat cttaatgtat gtaat                                    35

<210> SEQ ID NO 23
<211> LENGTH: 35
<212> TYPE: DNA
<213> ORGANISM: Glycine max

<400> SEQUENCE: 23
acattattag atgaaccgtg tatgtacata cattc                                    35
```

```
<210> SEQ ID NO 24
<211> LENGTH: 35
<212> TYPE: DNA
<213> ORGANISM: Glyince max

<400> SEQUENCE: 24
ttcaacaaag aaacgtggat aagaaatgtt tccta                              35

<210> SEQ ID NO 25
<211> LENGTH: 35
<212> TYPE: DNA
<213> ORGANISM: Glycine max

<400> SEQUENCE: 25
ttcaacaaag aaacgtagat aagaaatgtt tccta                              35

<210> SEQ ID NO 26
<211> LENGTH: 439
<212> TYPE: DNA
<213> ORGANISM: Glycine max

<400> SEQUENCE: 26
gaattttatt ttgaacgcct ttctgaagat tcattaactt ccattctggc accagaaatc   60
attataaatg ctatccttta attcttagct atgcgcttta tgtaacaata cgatttctat  120
tattattatt attattatta ttattattat tattattatt attattatta ttattattat  180 tatattttt  cctattttg gaaatatatt tctattttca aaataatata cttttattt   240 taattatata ttttaagttt aattactccg cactctgctt ttactaaaat ttttaattag  300
ttctctaaat ttttttaagt aagtttggat tctagaactt tacattaaat tcatctaact  360
caattcacaa gcatcctctg aatatatcat tatttaaagt attcagtaaa aaaaacaagt  420
cttatttaaa gtactgcca                                               439

<210> SEQ ID NO 27
<211> LENGTH: 378
<212> TYPE: DNA
<213> ORGANISM: Glycine max

<400> SEQUENCE: 27
aaataggcaa acaccgtat gaaaaatagg ttatcgttat tcataattta cttcagacac    60
tttatatttc tgttttctct taagaaaaaa aaaactaaaa caaatgtcg acagtagttg   120 tcaatacagt agcgtatgaa taaaggtttt ctgttgaata taacattatt attattatta  180
ttattattat tattattatt aatattagac tgtaaacgtt ttaattacta ctactttttt  240
actttatgaa ttttgtgagt aagttgatga tggacccta cttcaatgag attttaacca   300
ttaagcccac gattgactaa aggaatttat aggttcacac ttgtgaatga tgtagtcctt  360
gcctgttaag ttttgccc                                                378

<210> SEQ ID NO 28
<211> LENGTH: 23
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 28 gaatttatt ttgaacgcct ttc                                            23
```

```
<210> SEQ ID NO 29
<211> LENGTH: 23
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 29
gcagagtgcg gagtaattaa act                                              23

<210> SEQ ID NO 30
<211> LENGTH: 24
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 30
aaataggcaa aacaccgtat gaaa                                             24

<210> SEQ ID NO 31
<211> LENGTH: 21
<212> TYPE: DNA
<213> ORGANISM: Artificial Sequence
<220> FEATURE:
<223> OTHER INFORMATION: Other information: Description of artificial
      sequence: synthetic primer

<400> SEQUENCE: 31
gggcaaaact taacaggcaa g                                                21

<210> SEQ ID NO 32
<211> LENGTH: 23
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 32
agcgcatagc taagaattaa agg                                              23

<210> SEQ ID NO 33
<211> LENGTH: 23
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 33
agcgcacagc taagtattaa agg                                              23

<210> SEQ ID NO 34
<211> LENGTH: 20
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 34
taatattaga ctgtaaacgt                                                  20
```

```
<210> SEQ ID NO 35
<211> LENGTH: 19
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 35
tattattagg ctgtaaacg                                               19

<210> SEQ ID NO 36
<211> LENGTH: 35
<212> TYPE: DNA
<213> ORGANISM: Glycine max

<400> SEQUENCE: 36
gctatccttt aattcttagc tatgcgcttt atgta                             35

<210> SEQ ID NO 37
<211> LENGTH: 33
<212> TYPE: DNA
<213> ORGANISM: Glycine max

<400> SEQUENCE: 37
ttattattat taatattaga ctgtaaacgt ttt                               33

<210> SEQ ID NO 38
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 38
aaaagtgaat cttaat                                                  16

<210> SEQ ID NO 39
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 39
aaaagtcaat cttaat                                                  16

<210> SEQ ID NO 40
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 40
atgaaccgtg tatgta                                                  16

<210> SEQ ID NO 41
<211> LENGTH: 16
<212> TYPE: DNA
<213> ORGANISM: Artificial Sequence
<220> FEATURE:
<223> OTHER INFORMATION: Other information: Description of artificial
      sequence: synthetic probe
```

```
<400> SEQUENCE: 41
atgaactgtg tatgta                                                  16

<210> SEQ ID NO 42
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 42
tgtcacaaga gaaaagt                                                 17

<210> SEQ ID NO 43
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 43
attacataca ttaagat                                                 17

<210> SEQ ID NO 44
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 44
cacattatta gatgaac                                                 17

<210> SEQ ID NO 45
<211> LENGTH: 17
<212> TYPE: DNA
<213> ORGANISM: Artificial Sequence
<220> FEATURE:
<223> OTHER INFORMATION: Other information: Description of artificial
      sequence: synthetic probe

<400> SEQUENCE: 45
gaatgtatgt acataca                                                 17
```

METHODS AND COMPOSITIONS FOR SELECTING SOYBEAN PLANTS RESISTANT TO SOUTHERN ROOT KNOT NEMATODE

CROSS-REFERENCE TO RELATED APPLICATIONS

This application claims priority to U.S. Provisional Application No. 61/055,519, filed May 23, 2008, and to U.S. Provisional Application No. 60/963,836, filed Aug. 7, 2007.

INCORPORATION OF SEQUENCE LISTING

A sequence listing containing the file named "pa_01413.txt" which is 16.1 kilobytes (measured in MS-Windows®) and created on Aug. 1, 2008, comprises 45 nucleotide sequences, and is herein incorporated by reference in its entirety.

FIELD OF THE INVENTION

The present invention is in the field of plant breeding and disease resistance. More specifically, the invention includes a method for breeding soybean plants containing quantitative trait loci (QTL) associated with disease resistance to Southern Root Knot Nematode (SRKN), a disease associated with the pathogen *Meloidogyne incognita*. The invention further relates to the use of genetic markers to identify the QTL for disease resistance to the pathogen *Meloidogyne incognita*. The invention further includes germplasm and the use of germplasm containing QTL conferring disease resistance for introgression into elite germplasm in a breeding program for resistance to SRKN.

BACKGROUND OF THE INVENTION

Root-knot nematodes (*Meloidogyne* spp.) are plant pathogens that infect many hosts and cause extensive damage to crops throughout the world. In the southeastern United States, the Southern Root Knot Nematode (*Meloidogyne incognita*), herein referred to as SRKN, is a major pest of soybean (*Glycine max* (L)). Restrictions on the use of nematicides including cancellation of DBCP (1,2-dibromo3-chloropropane) and EDB (ethylene dibromine) have encouraged development of alternative methods of SRKN control (Harris et al. *Crop Sci.* 43:1848-1851 (2003)). Growing SRKN-resistant soybean cultivars is the most effective means of reducing losses in yield and growers' profits due to the parasite (Li et al., *Theor Appl Genet* 103:1167-1173 (2001)). Therefore, a number of SRKN-resistant cultivars have been developed (Ha et al., *Crop Science* 44:758-763 (2004)).

Both elite soybean varieties and accession germplasm have been examined for SRKN resistance. Two sources of SRKN resistance are PI 96354 and Palmetto. Phenotypic screening of 2,370 soybean accessions from the USDA Soybean Germplasm Collection (Urbana, Ill.) identified PI 96354 as the most highly resistant source in the collection (Luzzi, et al. *Crop Sci.* 27:258-262 (1987)). Crossing the highly SRKN resistant variety PI 96354 with the SRKN susceptible Bossier allowed for mapping a major quantitative trait loci (QTL) for SRKN resistance to linkage group (LG) O and a minor QTL to LG-G of the publicly available soybean genetic linkage map (Tamulonis et al., *Crop Sci.* 37: 1903-1909 (1997)). Forrest is another soybean variety which exhibits resistance to SRKN and has been used as a parental source of SRKN resistance in the development of soybean varieties. The ancestral source of SRKN resistance in Forrest and many other elite varieties is considered to be Palmetto (Ha et al. *Crop Sci.* 44:758-763 (2004)). A major SRKN resistance QTL Rmi was identified in studies with a cross of Forrest with the susceptible Bossier (Luzzi et al., *J Heredity* 85:484-486 (1994)). Pedigree analysis of forty-eight soybean varieties and genotyping using simple sequence repeats (SSRs) markers provided evidence that SRKN resistant varieties inherited a major SRKN resistant QTL (Rmi) on Linkage Group O from ancestral resistant sources (Ha et al. *Crop Sci.* 44:758-763 (2004)).

Breeding for SRKN resistant soybeans can be greatly facilitated by the use of marker-assisted selection for SRKN resistance QTL. Single nucleotide polymorphisms (SNPs) and (SSRs) can be used as genetic markers to locate QTL associated with SRKN resistance. SNPs are preferred a because technologies are available for automated, high-throughput screening with SNP marker platforms, which can decrease the time to select for and introgress SRKN resistance in soybean plants. Further, SNP markers are ideal because the likelihood that a particular SNP allele is derived from independent origins in the extant populations of a particular species is very low. As such, SNP markers are useful for tracking and assisting introgression of SRKN resistance alleles, particularly in the case of SRKN resistance haplotypes. SNP markers can be used to screen for SRKN resistance QTL on LG-O and LG-G of the soybean genetic linkage map (Ha et al., *Crop Sci.* 47(2) S73-S82 (2007)).

The present invention provides and includes methods and compositions for screening and selecting a soybean plant comprising the SRKN resistance QTL.

SUMMARY OF THE INVENTION

The present invention provides a method of introgressing an allele into a soybean plant comprising the steps of: (a) providing a population of soybean plants; (b) genotyping at least one soybean plant in the population with respect to a soybean genomic nucleic acid marker selected from the group comprising SEQ ID NOs: 1-4, 26 and 27; (c) selecting from the at least one soybean plant comprising at least one allele associated with SRKN resistance, wherein the SRKN resistance allele is selected from the group consisting of SEQ ID NOs: 21-25, 36 and 37. The invention further provides that the population of soybean plants can be derived by crossing at least one SRKN resistant soybean plant with at least one SRKN sensitive soybean plant.

The present invention further comprises an elite soybean plant produced by the method of (a) providing a population of soybean plants; (b) genotyping at least one soybean plant in the population with respect to a soybean genomic nucleic acid marker selected from the group comprising SEQ ID NOs: 1-4, 26 and 27; (c) selecting from the at least one soybean plant comprising at least one allele associated with SRKN resistance, wherein the SRKN resistance allele is selected from the group consisting of SEQ ID NOs: 21-25, 36 and 37. The invention further provides that the elite soybean plant can exhibit a transgenic trait wherein the transgenic trait is selected from the group consisting of herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistance, increased digestibility, improved processing traits, improved flavor, nitrogen fixation, hybrid seed production, and reduced allergenicity. In a further embodiment, the herbicide tolerance conferred is selected from the group consisting of glyphosate, dicamba, glufosinate, sulfonulurea, bromoxynil, 2,4,-Dichlorophenoxyacetic acid, and norflurazon herbicides. The methods provided by this invention can further comprise the step (d) of assaying the selected soybean plant for resistance to a SRKN-inducing pathogen. In certain embodiments of the methods, genotyping is effected in step (b) by an assay which is selected from the group consisting of single base extension (SBE), allele-specific primer extension sequencing (ASPE), DNA sequencing, RNA sequencing, micro-array based analyses, universal PCR, allele specific extension, hybridization, mass spectrometry, ligation, extension-ligation, and Flap-Endonuclease-mediated assays.

The invention further comprises a method of introgressing an allele into a soybean plant comprising: (a) providing a population of soybean plants, (b) screening the population with at least one nucleic acid marker and (c) selecting from the population one or more soybean plants comprising an SRKN resistance allele, wherein the SRKN resistance allele is an allele selected from the group consisting of an SRKN resistance locus where one or more alleles at one or more of their loci are selected from the group consisting of SRKN resistance allele 1, SRKN resistance allele 2, SRKN resistance allele 3, SRKN resistance allele 4, SRKN resistance allele 5, and SRKN resistance allele 6.

The invention further comprises an elite soybean plant produced by the method of: (a) providing a population of soybean plants, (b) screening the population with at least one nucleic acid marker and (c) selecting from the population one or more soybean plants comprising an SRKN resistance allele, wherein the SRKN resistance allele is an allele selected from the group consisting of an SRKN resistance locus where one or more alleles at one or more of their loci are selected from the group consisting of SRKN resistance allele 1, SRKN resistance allele 2, SRKN resistance allele 3, SRKN resistance allele 4, SRKN resistance allele 5, and SRKN resistance allele 6.

The soybean or elite soybean plants produced by any of the methods of this invention can further comprise a transgenic trait. The transgenic trait can be selected from the group consisting of herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistance, increased digestibility, improved processing traits, improved flavor, nitrogen fixation, hybrid seed production, and reduced allergenicity. The herbicide tolerance trait can be selected from the group consisting of glyphosate, dicamba, glufosinate, sulfonulurea, bromoxynil, 2,4-Dichlorophenoxyacetic acid, and norflurazon herbicides.

The present invention includes a substantially purified nucleic acid molecule comprising a nucleic acid sequence selected from the group consisting of SEQ ID NO: 1 through SEQ ID NO: 45 and complements thereof. These isolated nucleic acids can be used in practicing the methods of the invention. Isolated nucleic acid molecules for detecting a molecular marker representing a polymorphism in soybean DNA can comprise at least 15 nucleotides that include or are adjacent to the polymorphism, wherein the nucleic acid molecule is at least 90 percent identical to a sequence of the same number of consecutive nucleotides in either strand of DNA that include or are adjacent to the polymorphism, and wherein the molecular marker is selected from the group consisting of SEQ ID NOs: 1 through 4 and 26 through 27. The isolated nucleic acid can further comprise a detectable label or provide for incorporation of a detectable label. This detectable label can be selected from the group consisting of an isotope, a fluorophore, an antioxidant, a reductant, a nucleotide, and a hapten. This detectable label can be added to the nucleic acid by a chemical reaction or incorporated by an enzymatic reaction. Isolated nucleic acid molecules provided herein can comprise at least 16, 17, 18, or 20 nucleotides on either strand of the DNA that include or are adjacent to the polymorphism. In other embodiments, the isolated nucleic acid can hybridize to at least one allele of the molecular marker under stringent hybridization conditions.

The soybean plants selected by the methods of the invention may further exhibit increased grain yield in the presence of SRKN as compared to soybean plants lacking SRKN resistance alleles. In these methods, the selected one or more soybean plants may exhibit an increased grain yield of at least 0.5 Bu/A, 1.0 Bu/A or 1.5 Bu/A in the presence of SRKN as compared to plants lacking SRKN resistance alleles.

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 1. Listing of SNP markers for the SRKN resistance locus with the resistant and susceptible allele for each marker indicated. For marker NS0102683, there are two resistance alleles, A and G, wherein A is resistant and G is highly resistant.

FIG. 2. SNP Markers for detecting SRKN resistance. The resistant haplotype for SNP358 is TA and the resistant haplotype for SNP199 is AA. The haplotype from two polymorphisms at each marker can be used in selecting for SRKN resistance.

BRIEF DESCRIPTION OF NUCLEIC ACID SEQUENCES

SEQ ID NO: 1 is a genomic sequence derived from *Glycine max* associated with the SRKN resistance locus Rmi.

SEQ ID NO: 2 is a genomic sequence derived from *Glycine max* associated with the SRKN resistance locus Rmi.

SEQ ID NO: 3 is a genomic sequence derived from *Glycine max* associated with the SRKN resistance locus Rmi.

SEQ ID NO: 4 is a genomic sequence derived from *Glycine max* associated with the SRKN resistance locus Rmi.

SEQ ID NO: 5 is a forward PCR primer for amplifying SEQ ID NO: 1.

SEQ ID NO: 6 is a reverse PCR primer for amplifying SEQ ID NO: 1.

SEQ ID NO: 7 is a forward PCR primer for amplifying SEQ ID NO: 2.

SEQ ID NO: 8 is a reverse PCR primer for amplifying SEQ ID NO: 2.

SEQ ID NO: 9 is a forward PCR primer for amplifying SEQ ID NO: 3.

SEQ ID NO: 10 is a reverse PCR primer for amplifying SEQ ID NO: 3.

SEQ ID NO: 11 is a forward PCR primer for amplifying SEQ ID NO: 4.

SEQ ID NO: 12 is a reverse PCR primer for amplifying SEQ ID NO: 4.

SEQ ID NO: 13 is a probe for detecting the SRKN resistance locus of SEQ ID NO: 1.

SEQ ID NO: 14 is a second probe for detecting the SRKN resistance locus of SEQ ID NO: 1.

SEQ ID NO: 15 is a probe for detecting the SRKN resistance locus of SEQ ID NO: 2.

SEQ ID NO: 16 is a second probe for detecting the SRKN resistance locus of SEQ ID NO: 2.

SEQ ID NO: 17 is a probe for detecting the SRKN resistance locus of SEQ ID NO: 3.

SEQ ID NO: 18 is a second probe for detecting the SRKN resistance locus of SEQ ID NO: 3.

SEQ ID NO: 19 is a probe for detecting the SRKN resistance locus of SEQ ID NO: 4.

SEQ ID NO: 20 is a second probe for detecting the SRKN resistance locus of SEQ ID NO: 4.

SEQ ID NO: 21 is an SRKN resistance allele 1 corresponding to SEQ ID NO: 1.

SEQ ID NO: 22 is an SRKN resistance allele 2 corresponding to SEQ ID NO: 2.

SEQ ID NO: 23 is an SRKN resistance allele 3 corresponding to SEQ ID NO: 3.

SEQ ID NO: 24 is an SRKN resistance allele 4 corresponding to SEQ ID NO: 4.

SEQ ID NO: 25 is a second SRKN resistance allele motif corresponding to SEQ ID NO:4.

SEQ ID NO: 26 is a genomic sequence derived from *Glycine max* corresponding to the SRKN resistance locus Rmi.

SEQ ID NO: 27 is a genomic sequence derived from *Glycine max* corresponding to the SRKN resistance locus on LG-G.

SEQ ID NO: 28 is a forward PCR primer for amplifying SEQ ID NO: 26.

SEQ ID NO: 29 is a reverse PCR primer for amplifying SEQ ID NO: 26.

SEQ ID NO: 30 is a forward PCR primer for amplifying SEQ ID NO: 27.

SEQ ID NO: 31 is a reverse PCR primer for amplifying SEQ ID NO: 27.

SEQ ID NO: 32 is a probe for detecting the SRKN resistance locus of SEQ ID NO: 26.

SEQ ID NO: 33 is a second probe for detecting the SRKN resistance locus of SEQ ID NO: 26.

SEQ ID NO: 34 is a probe for detecting the SRKN resistance locus of SEQ ID NO: 27.

SEQ ID NO: 35 is a second probe for detecting the SRKN resistance locus of SEQ ID NO: 27.

SEQ ID NO: 36 is an SRKN resistance allele 5 corresponding to SEQ ID NO: 26.

SEQ ID NO: 37 is an SRKN resistance allele 6 corresponding to SEQ ID NO: 27.

SEQ ID NO: 38 is a hybridization probe for detecting the SRKN resistance locus of SEQ ID NO: 2.

SEQ ID NO: 39 is a second hybridization probe for detecting the SRKN resistance locus of SEQ ID NO: 2.

SEQ ID NO: 40 is a hybridization probe for detecting the SRKN resistance locus of SEQ ID NO: 3.

SEQ ID NO: 41 is a second hybridization probe for detecting the SRKN resistance locus of SEQ ID NO: 3.

SEQ ID NO: 42 is a forward single base extension probe for detecting the SRKN resistance locus of SEQ ID NO: 2.

SEQ ID NO: 43 is a reverse single base extension probe for detecting the SRKN resistance locus of SEQ ID NO: 2.

SEQ ID NO: 44 is a forward single base extension probe for detecting the SRKN resistance locus of SEQ ID NO: 3.

SEQ ID NO: 45 is a reverse single base extension probe for detecting the SRKN resistance locus of SEQ ID NO: 3.

DETAILED DESCRIPTION OF THE INVENTION

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press: New York, 2007. The nomenclature for DNA bases as set forth at 37 CFR §1.822 is used.

An "allele" refers to an alternative sequence at a particular locus; the length of an allele can be as small as 1 nucleotide base, but is typically larger. Allelic sequence can be denoted as nucleic acid sequence or as amino acid sequence that is encoded by the nucleic acid sequence.

A "locus" is a position on a genomic sequence that is usually found by a point of reference; e.g., a short DNA sequence that is a gene, or part of a gene or intergenic region. The loci of this invention comprise one or more polymorphisms in a population; i.e., alternative alleles present in some individuals.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In addition, the presence, absence, or variation in copy number of the preceding may comprise a polymorphism.

As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics. As used herein, "genetic marker" means polymorphic nucleic acid sequence or nucleic acid feature. A genetic marker may be represented by one or more particular variant sequences, or by a consensus sequence. In another sense, a "genetic marker" is an isolated variant or consensus of such a sequence.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "typing" refers to any method whereby the specific allelic form of a given soybean genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

As used herein, the phrase "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, "resistance allele" means the nucleic acid sequence that includes the polymorphic allele associated with resistance to SRKN.

As used herein, the term "soybean" means Glycine max and includes all plant varieties that can be bred with soybean, including wild soybean species.

As used herein, the term "comprising" means "including but not limited to".

As used herein, the term "elite line" means any line that has resulted from breeding and selection for superior agronomic performance. Non-limiting examples of elite soybean varieties that are commercially available to farmers or soybean breeders include AG00802, A0868, AG0902, A1923, AG2403, A2824, A3704, A4324, A5404, AG5903 and AG6202 (Asgrow Seeds, Des Moines, Iowa, USA); BPR0144RR, BPR 4077NRR and BPR 4390NRR (Bio Plant Research, Camp Point, Ill., USA); DKB17-51 and DKB37-51 (DeKalb Genetics, DeKalb, Ill., USA); and DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS 13-K2 (NK Division of Syngenta Seeds, Golden Valley, Minn., USA); 90M01, 91M30, 92M33, 93M11, 94M30, 95M30 and 97B52 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9 and S78-G6 (Syngenta Seeds, Henderson, Ky., USA). An elite plant is a representative plant from an elite variety.

The present invention provides SNP DNA markers useful for screening for the SRKN resistance QTL, located on Linkage Group O and Linkage Group G (Cregan et al., *Crop Sci.* 39:1464-1490 (1999)). SNP markers used to monitor the introgression of the SRKN resistance QTL Rmi on Linkage Group O include those selected from the group consisting of NS0094902, NS0097935, NS0135583, NS0102683, and SNP358. The SNP marker SNP199 is used to monitor the introgression of the SRKN resistance QTL on Linkage Group G. In the present invention, illustrative SRKN resistance locus Rmi SNP marker sequence (SEQ ID NO: 1) can be amplified using the primers indicated as SEQ ID NOs: 5 and 6, and detected with probes indicated as SEQ ID NOs: 13 or 14. Illustrative SRKN resistance locus Rmi SNP marker sequence (SEQ ID NO: 2) can be amplified using the primers indicated as SEQ ID NOs: 7 and 8, and detected with probes indicated as SEQ ID NOs: 15, 16, 38, 39, 42, or 43. Illustrative SRKN resistance locus Rmi SNP marker sequence (SEQ ID NO: 3) can be amplified using the primers indicated as SEQ ID NOs: 9 and 10, and detected with probes indicated as SEQ ID NOs: 17, 18, 40, 41, 44, or 45. Illustrative SRKN resistance locus Rmi SNP marker sequence (SEQ ID NO: 4) can be amplified using primers indicated as SEQ ID NOs: 11 and 12, and detected with probes indicated as SEQ ID NOs: 19 or 20. Illustrative SRKN resistance locus Rmi SNP marker sequence (SEQ ID NO: 26) can be amplified using primers indicated as SEQ ID NOs: 28 and 29, and detected with probes indicated as SEQ ID NOs: 32 or 33. Illustrative SRKN resistance locus on LG-G SNP marker sequence (SEQ ID NO: 27) can be amplified using primers indicated as SEQ ID NOs: 30 and 31, and detected with probes indicated as SEQ ID NOs: 34 or 35.

The present invention also provides a soybean plant comprising a nucleic acid sequence selected from the group consisting of SEQ ID NOs: 21-25, 36-37 and complements thereof. The present invention also provides a soybean plant comprising a nucleic acid sequence selected from the group consisting of SEQ ID NOs: 1-4, 25, and 26 fragments thereof, and complements of both. The present invention also provides a soybean plant comprising a nucleic acid sequence selected from the group consisting of SEQ ID NOs: 5-20 and 27-34, fragments thereof, and complements of both. In one aspect, the soybean plant comprises 2, 3, or 4 nucleic acid sequences selected from the group consisting of SEQ ID NOs: 21-25 and 36-37 and complements thereof. In another aspect, the soybean plant comprises 2, 3, or 4 nucleic acid sequences selected from the group consisting of SEQ ID NOs: 1-4, 26 and 27, fragments thereof, and complements of both. In a further aspect, the soybean plant comprises 2, 3, or 4 nucleic acid sequences selected from the group consisting of SEQ ID NOs: 5-20 and 27-34, fragments thereof, and complements of both.

As used herein, SRKN refers to any SRKN variant or isolate. A soybean plant of the present invention can be resistant to one or more nematodes capable of causing or inducing SRKN. In one aspect, the present invention provides plants resistant to SRKN as well as methods and compositions for screening soybean plants for resistance or susceptibility to SRKN, caused by the genus *Meloidogyne*. In a preferred aspect, the present invention provides methods and compositions for screening soybean plants for resistance or susceptibility to *Meloidogyne incognita*.

The present invention further provides that the selected plant is from the group consisting of members of the genus *Glycine*, more specifically from the group consisting of *Glycine arenaria*, *Glycine argyrea*, *Glycine canescens*, *Glycine clandestine*, *Glycine curvata*, *Glycine cyrtoloba*, *Glycine falcate*, *Glycine latifolia*, *Glycine latrobeana*, *Glycine max*, *Glycine microphylla*, *Glycine pescadrensis*, *Glycine pindanica*, *Glycine rubiginosa*, *Glycine soja*, *Glycine* sp., *Glycine stenophita*, *Glycine tabacina* and *Glycine tomentella*

Plants of the present invention can be a soybean plant that is very resistant, resistant, substantially resistant, mid-resistant, comparatively resistant, partially resistant, mid-susceptible, or susceptible.

In a preferred aspect, the present invention provides a soybean plant to be assayed for resistance or susceptibility to SRKN by any method to determine whether a soybean plant is very resistant, resistant, substantially resistant, mid-resistant, comparatively resistant, partially resistant, mid-susceptible, or susceptible.

In one aspect, the present invention provides methods and compositions for screening soybean plants for resistance, immunity, or susceptibility to SRKN, caused by the species *Meloidogyne incognita*. In a preferred aspect, the present invention provides methods and compositions for screening soybean plants for resistance, immunity, or susceptibility to *Meloidogyne incognita*. Soybean plants are phenotyped and scored for resistance, immunity, or susceptibility to SRKN based upon number of galls or egg masses (Taylor and Sasser, *Biology, identification and control of root-knot nematodes (Meloidogyne species): A cooperative publication of the Department of Plant Pathology*. p. 111 (1978)).

The SRKN resistance QTL of the present invention may be introduced into an elite *Glycine max* line. An "elite line" is any line that has resulted from breeding and selection for superior agronomic performance.

The SRKN resistance QTL of the present invention may also be introduced into an elite *Glycine max* transgenic plant that contains one or more genes for herbicide tolerance, increased yield, insect control, fungal disease resistance, virus resistance, nematode resistance, bacterial disease resistance, *mycoplasma* disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in *Glycine max*.

A disease resistant QTL allele or alleles can be introduced from any plant that contains that allele (donor) to any recipient soybean plant. In one aspect, the recipient soybean plant can contain additional SRKN resistant loci. In another aspect, the recipient soybean plant can contain a transgene. In another aspect, while maintaining the introduced QTL, the genetic contribution of the plant providing the disease resistant QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the SRKN resistant locus or loci of interest.

It is further understood that a soybean plant of the present invention may exhibit the characteristics of any relative maturity group. In an aspect, the maturity group is selected from the group consisting of 000, 00, 0, 1, 2, 3, 4, 5, 6, 7, 8, 9, and 10.

An allele of a QTL can comprise multiple genes or other genetic factors even within a contiguous genomic region or linkage group, such as a haplotype. As used herein, an allele of a resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be pest resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular SRKN resistance locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

The present invention also provides a container of soybean in which greater than 50%, 60%, 70%, 80%, 90%, 95%, or 99% of the seeds comprising the SRKN resistant loci where one or more alleles at the loci are selected from the group consisting of SRKN resistant allele 1, SRKN resistance allele 2, SRKN resistance allele 3, or SRKN resistance allele 4.

The container of soybean seeds can contain any number, weight, or volume of seeds. For example, a container can contain at lest, or greater than, about 10, 25, 50, 100, 200, 300, 400, 500, 600, 700, 80, 90, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of soybean seeds can be any container available in the art. For example, a container can be a box, a bag, a can, a packet, a pouch, a tape roll, a pail, or a tube.

In another aspect, the seeds contained in the containers of soybean seeds can be treated or untreated soybean seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

The disease resistant effect of the QTL can vary based on the individual genotype and on the environmental conditions in which the disease resistance effect is measured. It is within the skill of those in the art of plant breeding and without undue experimentation to use the methods described herein to select from a population of plants or from a collection of parental genotypes those that when containing a disease locus result in enhanced disease resistance relative to the genotype.

The present invention includes a method of introgressing an allele into a soybean plant comprising (A) crossing at least one first soybean plant comprising a nucleic acid sequence selected from the group consisting of SEQ ID NOs: 21 through 25, 36 and 37 with at least one second soybean plant in order to form a population, (B) screening the population with one or more nucleic acid markers to determine if one or more soybean plants from the population contains the nucleic acid sequence, and (C) selecting from the population one or more soybean plants comprising a nucleic acid sequence selected from the group consisting of SEQ ID NOs: 21 through 25, 36, and 37.

The present invention includes a method of introgressing an allele into a soybean plant comprising: (A) crossing at least one SRKN resistant soybean plant with at least one SRKN sensitive plant in order to form a population; (B) screening said population with one or more nucleic acid markers to determine if one or more soybean plants from said population contains the SRKN resistance locus on LG-O or LG-G.

The present invention includes isolated nucleic acid molecules. Such molecules include those nucleic acid molecules capable of detecting a polymorphism genetically or physically linked to a SRKN locus. Such molecules can be referred to as markers Additional markers can be obtained that are linked to SRKN resistance locus by available techniques. In one aspect, the nucleic acid molecule is capable of detecting the presence or absence of a marker located less than 30, 25, 20, 15, 10, 5, 2, or 1 centimorgans from the SRKN resistance locus. In another aspect, a marker exhibits a LOD score of 2 or greater, 3 or greater, or 4 or greater with SRKN measuring using Qgene Version 2.23 (1996) and default parameters. In another aspect, the nucleic acid molecule is capable of detecting a marker in a locus selected from the group SRKN resistance locus Rmi. In another aspect, the nucleic acid molecule is capable of detecting a marker in the SRKN resistance QTL. In a further aspect, a nucleic acid molecule is selected from the group consisting of SEQ ID NOs: 1 through 4, 26 and 27, fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO: 1 through SEQ ID NO: 45 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 1 through SEQ ID NO: 45 or complements or fragments of either under high stringency conditions. In one aspect of the present invention, a preferred marker nucleic acid molecule of the present invention has the nucleic acid sequence set forth in SEQ ID NO: 1 through SEQ ID NO: 45 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 1 through SEQ ID NO: 45 or complement thereof or fragments of either. In a further aspect of the present invention, a preferred marker nucleic acid molecule of the present invention shares between 95% and 100% sequence identity with the sequence set forth in SEQ ID NO: 1 through SEQ ID NO: 45 or complement thereof or fragments of either. In a more preferred aspect of the present invention, a preferred marker nucleic acid molecule of the present invention shares between 98% and 100% sequence identity with the nucleic acid sequence set forth in SEQ ID NO: 1 through SEQ ID NO: 45 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual,* 2nd Edition, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 Nucl. Acids Res. 12:203-213; and Wetmur et al. 1968 J. Mol. Biol. 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 1 to SEQ ID NO: 45 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Markers, such as single sequence repeat markers (SSR), AFLP markers, RFLP markers, RAPD markers, phenotypic markers, SNPs, isozyme markers, microarray transcription profiles that are genetically linked to or correlated with alleles of a QTL of the present invention can be utilized (Walton, 1993; Burow et al. 1988). Methods to identify such markers are known in the art.

The detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258, 017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

In a preferred method for detecting polymorphisms, SNPs and Indels can be detected by methods disclosed in U.S. Pat. Nos. 5,210,015; 5,876,930 and 6,030,787 in which an oligonucleotide probe having a 5'fluorescent reporter dye and a 3'quencher dye covalently linked to the 5' and 3' ends of the probe. When the probe is intact, the proximity of the reporter dye to the quencher dye results in the suppression of the reporter fluorescence, for example, by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

A useful assay is available from AB Biosystems as the Taqman® assay which employs four synthetic oligonucleotides in a single reaction that concurrently amplifies the soybean genomic DNA, discriminates between the alleles present, and directly provides a signal for discrimination and detection. Two of the four oligonucleotides serve as PCR primers and generate a PCR product encompassing the polymorphism to be detected. Two others are allele-specific fluorescence-resonance-energy-transfer (FRET) probes. In the assay, two FRET probes bearing different fluorescent reporter dyes are used, where a unique dye is incorporated into an oligonucleotide that can anneal with high specificity to only one of the two alleles. Useful reporter dyes include, but are not limited to, 6-carboxy-4,7,2',7'-tetrachlorofluorecein (TET), 2'-chloro-7'-phenyl-1,4-dichloro-6-carboxyfluorescein (VIC) and 6-carboxyfluorescein phosphoramidite (FAM). A useful quencher is 6-carboxy-N,N,N',N'-tetramethylrhodamine (TAMRA). Additionally, the 3'end of each FRET probe is chemically blocked so that it can not act as a PCR primer. Also present is a third fluorophore used as a passive reference, e.g., rhodamine X (ROX) to aid in later normalization of the relevant fluorescence values (correcting for volumetric errors in reaction assembly). During each cycle of the PCR, the FRET probes anneal in an allele-specific manner to the template DNA molecules. Annealed (but not non-annealed) FRET probes are degraded by TAQ DNA polymerase as the enzyme encounters the 5' end of the annealed probe, thus releasing the fluorophore from proximity to its quencher, wherein the fluorescence of each of the two fluorescers, as well as that of the passive reference, is determined fluorometrically. The normalized intensity of fluorescence for each of the two dyes will be proportional to the amounts of each allele initially present in the sample, and thus the genotype of the sample can be inferred.

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes which are closely linked alleles inherited as a unit.

The genetic linkage of additional marker molecules can be established by a gene mapping model such as, without limitation, the flanking marker model reported by Lander et al. (Lander et al., *Genetics*, 121:185-199 (1989)), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990)). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 Genetics, 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 Theor. Appl. Genet. 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted x exotic) and generally yield greatly reduced linkage distances. Wide crosses will usually provide segregating populations with a relatively large array of polymorphisms when compared to progeny in a narrow cross (adapted x adapted).

An $F_2$ population is the first generation of selfing. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al. 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

Breeding lines can be tested and compared to appropriate standards in environments representative of the commercial target area(s) for two or more generations. The best lines are candidates for new commercial cultivars; those still deficient in traits may be used as parents to produce new populations for further selection.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, *In: Soybeans: Improvement, Production and Uses,* 2nd Edition, *Manograph.,* 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

As used herein, a "nucleic acid molecule", be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al. 1987 Science 238:336-340; Albarella et al., European Patent 144914), chemical labels (Sheldon et al., U.S. Pat. No. 4,582,789; Albarella et al., U.S. Pat. No. 4,563, 417), modified bases (Miyoshi et al., European Patent 119448).

Having now generally described the invention, the same will be more readily understood through reference to the following examples which are provided by way of illustration, and are not intended to be limiting of the present invention, unless specified.

EXAMPLES

Example 1

SRKN Resistance Marker Discovery

SNP markers for the SRKN resistance QTL Rmi were identified by screening nucleic acid sequence flanking the Rmi locus in linkage group (LG) O in SRKN resistant and susceptible soybean lines. FIG. 1 summarizes the markers, their chromosome positions, the resistance and susceptible alleles, and the position of the SNP for each marker. FIG. 1 also provides primers and probes for the detection of the SNPs.

Example 2

Validation of SRKN Resistance SNP Markers in Publicly Available Germplasm

Soybean plants were phenotyped and scored according to the number of galls or egg masses present on the plant roots (Table 1). The greater the number of galls or egg masses, the more susceptible a plant is. The average gall index was then calculated and plants were assigned a SRKN rating of resistant, moderately resistant, moderately susceptible, or susceptible (Table 2).

In order to test the utility and predictability of the SRKN resistance markers of the present invention, 16 publicly available soybean lines with reported resistance and susceptibility reactions to SRKN were genotyped (Table 3). The haplotypes of the known resistant and susceptible varieties were found to be consistent using the SNP markers NS0094902, NS0097935, NS0135583, and NS0102683. The four SNP markers were found to be predictive of SRKN resistance in publicly available soybean germplasm.

Table 4 provides further validation of the four SNP markers. Fourteen public entries with reported SRKN resistance responses were genotyped. In addition, Palmetto was used as the SRKN resistant control and a SRKN susceptible line was used as a negative control. By using the four SNP markers, the haplotypes of twelve of the varieties were found to be consistent with that of the resistant control. One variety, G93-9223, had a different allelic state at only one of the markers, NS0102683. Two varieties, Musen and LS97-1610, had genotypes corresponding to the susceptible type. SRKN reaction was based on reported reaction rather than phenotyping in this example. However, the SNP markers were predictive of the SRKN reaction of the majority of lines and have utility in predicting soybean SRKN reactions.

Five public entries with reported SRKN susceptibility were genotyped (Table 5) with Palmetto as the SRKN resistant control and a susceptible line as the negative control. The haplotypes of the five entries were found to be consistent with that of the susceptible control.

Four SNP markers, NS0094902, NS0097935, NS0135583, and NS0102683, were found to be predictive of the SRKN QTL (Rmi) in public soybean varieties.

TABLE 1

Gall index used in phenotypic analysis for SRKN (Taylor and Sasser, 1978).

| Index Score | Number of galls or egg masses |
|---|---|
| 0 | 0 |
| 1 | 1 to 2 |
| 2 | 3 to 10 |
| 3 | 11 to 30 |
| 4 | 31 to 100 |
| 5 | >100 |

TABLE 2

SRKN disease rating scale. Ratings are resistant (R), Moderately Resistant (MR), Moderately Susceptible (MS), and Susceptible (S).

| SRKN rating | Gall Index |
|---|---|
| R | Average Gall Index <3.2 |
| MR | Average Gall Index 3.2 to <3.5 |
| MS | Average Gall Index 3.5 to <4.0 |
| S | Average Gall index 4.0+ |

TABLE 3

Validation of SRKN resistance SNP markers for detecting the presence or absence of the Rmi QTL on LG-O and the corresponding SRKN disease phenotypic responses. The varieties CNS, S-100, Palmetto, and Bragg are used as a resistant (R) and susceptible (S) panel to assess the efficacy of the SNP markers in differentiating resistant from susceptible in historical R and S soybean lines.

| Entry | SRKN | NS0094902 | NS0097935 | NS0135583 | NS0102683 |
|---|---|---|---|---|---|
| CNS | S | TTATCAATTAT | CC | TT | AA |
| S-100 | S | TTATCAATTAT | CC | TT | AA |
| Palmetto | R | ********** | GG | CC | AA |
| Bragg | R | ********** | GG | CC | AA |
| Lee | S | TTATCAATTAT | CC | TT | AA |
| Dyer | S | TTATCAATTAT | CC | TT | AA |
| Pickett71 | S | TTATCAATTAT | CC | TT | AA |
| Hutcheson | S | TTATCAATTAT | CC | TT | AA |
| Forrest | R | ********** | GG | CC | AA |
| Braxton | R | ********** | GG | CC | AA |
| Hartwig | R | ********** | GG | CC | AA |
| Manokin | R | ********** | GG | CC | AA |
| Dillon | R | ********** | GG | CC | AA |
| C6738 | R | ********** | GG | CC | AA |
| Cook | R | ********** | GG | CC | AA |
| Benning | R | ********** | GG | CC | AA |

TABLE 4

Validation of SRKN resistance SNP markers for detecting the presence or absence of the Rmi QTL on LG-O and the corresponding SRKN disease phenotypic responses, with Palmetto as the control for SRKN resistance and an SRKN susceptible line as a negative control.

| Entry | SRKN | NS0094902 | NS0097935 | NS0135583 | NS0102683 |
|---|---|---|---|---|---|
| Palmetto | R | ********** | GG | CC | AA |
| Susceptible Type | S | TTATCAATTAT | CC | TT | AA |
| Accomac | R | ********** | GG | CC | AA |
| Boggs | R | ********** | GG | CC | AA |

TABLE 4-continued

Validation of SRKN resistance SNP markers for detecting the presence or absence of the Rmi QTL on LG-O and the corresponding SRKN disease phenotypic responses, with Palmetto as the control for SRKN resistance and an SRKN susceptible line as a negative control.

| Entry | SRKN | NS0094902 | NS0097935 | NS0135583 | NS0102683 |
|---|---|---|---|---|---|
| Bryan | R | ********** | GG | CC | AA |
| Delsoy5710 | R | ********** | GG | CC | AA |
| G93-9106 | R | ********** | GG | CC | AA |
| G93-9223 | R | ********** | GG | CC | AG |
| LS94-3207 | R | ********** | GG | CC | AA |
| LS97-1610 | R | TTATCAATTAT | CC | TT | AA |
| LS97-3004 | R | ********** | GG | CC | AA |
| MUSEN | R | TTATCAATTAT | CC | TT | AA |
| S96-2692 | R | ********** | GG | CC | AA |
| Santee | R | ********** | GG | CC | AA |
| Stonewall | R | ********** | GG | CC | AA |
| NKS75-55 | R | ********** | GG | CC | AA |

TABLE 5

Validation of SRKN resistance SNP markers for detecting the presence or absence of the Rmi QTL on LG-O and the corresponding SRKN disease phenotypic responses, with Palmetto as the control for SRKN resistance and an SRKN susceptible line as negative control.

| Entry | SRKN | NS0094902 | NS0097935 | NS0135583 | NS0102683 |
|---|---|---|---|---|---|
| Palmetto | R | ********** | GG | CC | AA |
| Susceptible Type | S | TTATCAATTAT | CC | TT | AA |
| LS97-1631 | S | TTATCAATTAT | CC | TT | AA |
| Anand | S | TTATCAATTAT | CC | TT | AA |
| N94-552 (NCROY) | S | TTATCAATTAT | CC | TT | AA |
| NC RALEIGH | S | TTATCAATTAT | CC | TT | AA |
| S97-1688 | S | TTATCAATTAT | CC | TT | AA |

Example 3

Validation of SRKN Resistance SNP Markers in Monsanto Proprietary Lines

The SRKN resistance SNP markers were validated using Monsanto proprietary lines with known resistance and susceptibility reactions to SRKN disease. Eight MR/R varieties (Table 6) and 17 susceptible varieties (Table 7) were used. Disease ratings are based on average gall index scores as previously described in Table 2. In this example, phenotyping was conducted, and SRKN classification was based on either greenhouse testing or greenhouse testing with field testing.

Eight Monsanto proprietary varieties were phenotyped. Based on gall index ratings, these lines were classified as resistant/moderately resistant. Leaf tissue was genotyped. The haplotype of the eight varieties were found to be consistent with that of the resistant control Palmetto (Table 6).

Seventeen Monsanto proprietary varieties were phenotyped and rated as susceptible based on gall index ratings. Leaf tissue was genotyped, and the haplotype of the 17 varieties was found to be consistent with that of the susceptible type control (Table 7).

The four SNP markers were found to be useful for detecting the SRKN resistance QTL (Rmi) in Monsanto proprietary lines.

TABLE 6

Validation of SRKN resistance SNP markers for detecting for the presence and absence of the Rmi QTL on LG-O and the corresponding SRKN disease phenotypic responses, with Palmetto as the control for SRKN resistance and an SRKN susceptible line as negative control.

| Entry | SRKN | NS0094902 | NS0097935 | NS0135583 | NS010268 |
|---|---|---|---|---|---|
| Palmetto | R | ********** | GG | CC | AA |
| Susceptible Type | S | TTATCAATTAT | CC | TT | AA |
| AG5402 | R/MR | ********** | GG | CC | AA |
| DKB64-51 | R/MR | ********** | GG | CC | AA |
| H5218 | R/MR | ********** | GG | CC | AA |
| H6372 | R/MR | ********** | GG | CC | AG |
| H7440 | R/MR | ********** | GG | CC | AA |
| H5050RR | R/MR | ********** | GG | CC | AA |
| H6104RR | R/MR | ********** | GG | CC | AA |
| H7242RR | R/MR | ********** | GG | CC | AA |

TABLE 7

Validation of SRKN resistance markers for detecting for the presence and absence of the Rmi QTL on LG-O and the corresponding SRKN phenotypic responses of the Monsanto entries, with Palmetto as the control for SRKN resistance and an SRKN susceptible line as negative control.

| Entry | SRKN | NS0094902 | NS0097935 | NS0135583 | NS0102683 |
|---|---|---|---|---|---|
| Palmetto | R | ********** | GG | CC | AA |
| Susceptible Type | S | TTATCAATTAT | CC | TT | AA |
| MV0009 | S | TTATCAATTAT | CC | TT | AA |
| MV0010 | S | TTATCAATTAT | CC | TT | AA |
| MV0011 | S | TTATCAATTAT | CC | TT | AA |
| MV0012 | S | TTATCAATTAT | CC | TT | AA |
| MV0013 | S | TTATCAATTAT | CC | TT | AA |
| MV0014 | S | TTATCAATTAT | CC | TT | AA |
| MV0015 | S | TTATCAATTAT | CC | TT | AA |
| MV0016 | S | TTATCAATTAT | CC | TT | AA |
| MV0017 | S | TTATCAATTAT | CC | TT | AA |
| MV0018 | S | TTATCAATTAT | CC | TT | AA |
| MV0019 | S | TTATCAATTAT | CC | TT | AA |
| MV0020 | S | TTATCAATTAT | CC | TT | AA |
| MV0021 | S | TTATCAATTAT | CC | TT | AA |
| MV0022 | S | TTATCAATTAT | CC | TT | AA |
| MV0023 | S | TTATCAATTAT | CC | TT | AA |
| MV0024 | S | TTATCAATTAT | CC | TT | AA |
| MV0025 | S | TTATCAATTAT | CC | TT | AA |

Example 4

Ability to Distinguish SRKN Resistance Haplotype from Different Resistance Sources Two sources for SRKN resistance are Palmetto and PI96354. The SNP markers of the present invention can be used to distinguish between Palmetto and PI 96354 as the source of the SRKN resistance QTL (Rmi) (Table 8). The information provided by the markers can be useful in pedigree analyses.

TABLE 8

Validation of SRKN resistance SNP markers for differentiation of the two sources of SRKN resistance, Palmetto and PI 96354.

| Entry | SRKN | NS0094902 | NS0097935 | NS0135583 | NS0102683 |
|---|---|---|---|---|---|
| Susceptible Type | S | TTATCAATTAT | CC | TT | AA |
| Palmetto | R | *********** | GG | CC | AA |
| PI 96354 | VR | TTATCAATTAT | CC | TT | GG |

Example 5

Additional SNP Markers for SRKN Resistance

SNP markers linked to SRKN resistance QTL on LG-O and LG-G were developed through the use of bacterial artificial chromosome (BAC) ends and SSR-containing genomic DNA clones. Three SNPs were identified in Satt358 source-sequences located near the major SRKN resistance QTL on LG-O. Three SNPs were identified in Satt199 source-sequences located near the minor SRKN resistance QTL on LG-G.

SNP genotype analysis was performed with 94 F2 plants from the cross of PI96354 x Bossier. DNA was extracted from individual parental genotypes and individual field-grown F2 plants. F2:3 lines were evaluated in the greenhouse for SRKN galling.

A direct hybridization (DH) assay was developed and optimized using SNP358 from Satt358 source sequence on LG-O. Allele-specific oligonucleotide probes corresponding to each of PI 96354 and Bossier sequence variants were designed so that the two polymorphic bases at the 83 and 91 base position were included in the probe. The ASO358-TA probe was specific for the PI 96354 haploype and the ASO358-AG probe was specific for the Bossier haplotype. For the minor SRKN resistance QTL on LG-G, a DH assay was developed with SNP199 from the Satt199 source sequence of LG-G. The ASO199-AA probe was specific for the PI 96354 haplotype and the ASO199-TG probe was specific for the Bossier haplotype. The effectiveness of SNP358 and SNP199 were compared with their respective SSR markers, Satt358 and Satt199 by assaying 12 SRKN resistant and 12 SRKN susceptible soybean lines. Genotyping was conducted by a multiplex assay in which reaction specific microspheres fluoresce at different frequencies. Table 9 provides the results of the assays. Eleven of the 12 SRKN resistant lines carrying a 200-bp allele at Satt358 have approximately a 10x higher positive signal for the ASO358-TA probe specific to the PI 96354 allele (resistant) than the ASO358-AG probe specific to the Bossier allele (susceptible). All SRKN susceptible lines carrying the 192-bp allele at Satt358 had a positive signal for the Bossier-specific ASO358-AG probe. Susceptible soybean line FC 33243 has a unique haplotype (AA) at SNP358. Therefore, SNP358 has three SNP haplotypes TA, AG, and AA in 24 soybean lines. FIG. 2 provides the SNP markers and resistance haplotypes.

TABLE 9

Comparison between simple sequence repeat (SSR) markers and single nucleotide polymorphism (SNP) markers on linkage group-O (LG-O) and LG-G in SRKN resistant and susceptible soybean lines.

| Line | SRKN | Satt358 | MFI[1] SNP358 AS0358-TA | MFI SNP358 AS0358-AG | Satt199 | MFI SNP199 AS0199-AA | MFI SNP199 AS0199-TG |
|---|---|---|---|---|---|---|---|
| PI 96354 | HR | 200 | 1740 | 52 | 200 | 1781 | 126 |
| Benning | R | 200 | 1633 | 53 | 159 | 32 | 1440 |
| Bragg | R | 200 | 1698 | 277 | 159 | 30 | 1796 |
| Centennial | R | 200 | 1569 | 65 | 159 | 49 | 1747 |
| Cobb | R | 200 | 1687 | 46 | 200 | 1730 | 149 |
| Forrest | R | 200 | 2569 | 63 | 159 | 46 | 1512 |
| Gregg | R | 200/192 | 1032 | 2004 | 159 | 29 | 1596 |
| Hartwig | R | 200 | 1776 | 242 | 159 | 71 | 2216 |
| Jackson | R | 200 | 1682 | 156 | 170 | 29 | 1465 |
| Lamer | R | 200 | 1113 | 47 | 159 | 31 | 1118 |
| Palmetto | R | 200 | 1517 | 130 | 170 | 34 | 1541 |
| Perrin | R | 200 | 1518 | 38 | 159 | 39 | 1555 |
| Bossier | S | 192 | 66 | 1649 | 159 | 56 | 1934 |
| CNS | S | 200192 | 33 | 2200 | 162 | 39 | 1585 |
| Dyer | S | 200192 | 28 | 2309 | 159 | 27 | 1714 |
| FC 33243 | S | 160 | 182 | 247 | 200 | 1864 | 205 |
| Gasoy17 | S | 192 | 55 | 2592 | 200 | 1879 | 215 |

TABLE 9-continued

Comparison between simple sequence repeat (SSR) markers and single nucleotide polymorphism (SNP) markers on linkage group-O (LG-O) and LG-G in SRKN resistant and susceptible soybean lines.

| Line | SRKN | Satt358 | MFI[1] SNP358 AS0358- TA | MFI SNP358 AS0358- AG | Satt199 | MFI SNP199 AS0199- AA | MFI SNP199 AS0199- TG |
|---|---|---|---|---|---|---|---|
| Hutcheson | S | 192 | 88 | 2082 | 159 | 75 | 1622 |
| Johnston | S | 192 | 38 | 2132 | 159 | 39 | 1665 |
| Lee | S | 192 | 34 | 2232 | 159 | 29 | 1661 |
| S-100 | S | 192 | 108 | 2581 | 159 | 78 | 2064 |
| Tokyo | S | 192 | 42 | 2435 | 159 | 35 | 1767 |
| Volstate | S | 192 | 77 | 2520 | 200 | 2071 | 241 |
| Young | S | 192 | 71 | 2375 | 159 | 33 | 1802 |

[1]MFI = Mean Fluorescence Intensity

Example 6

Oligonucleotide Hybridization Probes Useful for Detecting Soybean Plants with SRKN Resistance Loci Oligonucleotides can also be used to detect or type the polymorphisms associated with SRKN resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization. Exemplary oligonucleotides for use in hybridization-based SNP detection are provided in Table 10. These oligonucleotides can be detectably labeled with radioactive labels, fluorophores, or other chemiluminescent means to facilitate detection of hybridization to samples of genomic or amplified nucleic acids derived from one or more soybean plants using methods known in the art.

TABLE 10

Oligonucleotide Hybridization Probes

| Marker | Marker SEQ ID | SNP Position | Hybridization Probe | SEQ ID Probe |
|---|---|---|---|---|
| NS0097935 | 2 | 346 | AAAAGTGAATCTTAAT | 38 |
| NS0097935 | 2 | 346 | AAAAGTCAATCTTAAT | 39 |
| NS0135583 | 3 | 730 | ATGAACCGTGTATGTA | 40 |
| NS0135583 | 3 | 730 | ATGAACTGTGTATGTA | 41 |

Example 7

Oligonucleotide Probes Useful for Detecting Soybean Plants with SRKN Resistance Loci by Single Base Extension Methods Oligonucleotides can also be used to detect or type the polymorphisms associated with SRKN resistance disclosed herein by single base extension (SBE)-based SNP detection methods. Exemplary oligonucleotides for use in SBE-based SNP detection are provided in Table 11. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in FIG. 1 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 11

Probes (extension primers) for Single Base Extension (SBE) assays.

| Marker | Marker SEQ ID | SNP Position | Probe (SBE) | Probe SEQ ID |
|---|---|---|---|---|
| NS0097935 | 2 | 346 | TGTCACAAGAGAAAAGT | 42 |
| NS0097935 | 2 | 346 | ATTACATACATTAAGAT | 43 |
| NS0135583 | 3 | 730 | CACATTATTAGATGAAC | 44 |
| NS0135583 | 3 | 730 | GAATGTATGTACATACA | 45 |

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A method of introgressing an allele into a soybean plant comprising:
   a. Providing a population of soybean plants;
   b. Genotyping at least one soybean plant in the population with respect to a soybean genomic nucleic acid marker selected from the group comprising SEQ ID NOs: 1-4, 26 and 27; and
   c. Selecting from the population at least one soybean plant comprising at least one allele associated with Southern Root Knot Nematode (SRKN) resistance, wherein the SRKN resistance allele is selected from the group consisting of SEQ ID NOs: 21-25, 36 and 37.

2. The method of claim 1, wherein the population is derived by crossing at least one SRKN resistant soybean plant with at least one SRKN sensitive soybean plant to form a population.

3. The method of claim 1, wherein the selected soybean plants exhibit a resistant reaction rating to SRKN of no worse than about 3.5.

4. The method according to claim 1, further comprising the step (d) of assaying the selected soybean plant for resistance to a SRKN-inducing pathogen.

5. The method of claim 1, wherein the genotype is determined by an assay which is selected from the group consisting of single base extension (SBE), allele-specific primer extension sequencing (ASPE), DNA sequencing, RNA sequencing, micro-array based analyses, universal PCR, allele specific extension, hybridization, mass spectrometry, ligation, extension-ligation, and Flap-Endonuclease-mediated assays.

6. The method of claim 1 wherein the soybean genomic nucleic acid marker is SEQ ID NO: 3.

7. A method of introgressing an allele into a soybean plant comprising:
   a. Providing a population of soybean plants;
   b. Screening the population with at least one nucleic acid marker selected from the group consisting of SEQ ID NO: 1-4, 27, and 37; and c. Selecting from the population one or more soybean plants comprising an Southern Root Knot Nematode (SRKN) [Southern Root Knot Nematode] resistance allele, wherein the SRKN [Southern Root Knot Nematode resistance] allele is selected from the group consisting of SRKN resistance allele 1, SRKN resistance allele 2, SRKN resistance allele 3, SRKN resistance allele 4, SRKN resistance allele 5, and SRKN resistance allele 6.

8. The method of claim 7 wherein the population is derived by crossing at least one SRKN resistant soybean plant with at least one SRKN sensitive soybean plant to form a population.

9. The method according to claim 7, wherein the selected soybean plants exhibit a resistant reaction rating to SRKN of no worse than about 3.5.

10. The method according to claim 7, further comprising the step (d) of assaying the selected soybean plant for resistance to a SRKN-inducing pathogen.

11. The method of claim 7, wherein the genotype is determined by an assay which is selected from the group consisting of single base extension (SBE), allele-specific primer extension sequencing (ASPE), DNA sequencing, RNA sequencing, micro-array based analyses, universal PCR, allele specific extension, hybridization, mass spectrometry, ligation, extension-ligation, and Flap-Endonuclease-mediated assays.

12. The method of claim 7 wherein the nucleic acid markers are selected from the group consisting of SEQ ID NOs: 1-4, 26 and 27.

13. The method according to claim 7, wherein the selected one or more soybean plants exhibit increased grain yield in the presence of SRKN as compared to soybean plants lacking SRKN resistance alleles.

14. The method according to claim 7, wherein the selected one or more soybean plants exhibit an increased grain yield of at least 0.5 Bu/A in the presence of SRKN as compared to plants lacking SRKN resistance alleles.

15. The method according to claim 7, wherein the selected one or more soybean plants exhibit an increased grain yield of at least 1.0 Bu/A in the presence of SRKN as compared to plants lacking SRKN resistance alleles.

16. The method according to claim 7, wherein the selected one or more soybean plants exhibit an increased grain yield of at least 1.5 Bu/A in the presence of SRKN as compared to plants lacking SRKN resistance alleles.

17. A method of identifying an SRKN resistance allele in a soybean plant comprising detecting a locus associated with a SNP marker selected from the group consisting of SEQ ID NOs: 1-4, 26 and 27.

\* \* \* \* \*